US005569222A

United States Patent [19]

Haselhorst et al.

[11] Patent Number: 5,569,222
[45] Date of Patent: Oct. 29, 1996

[54] ADAPTER FOR A VARIETY OF TUBES HAVING VARIOUS DIAMETERS AND A METHOD OF USING THE ADAPTER

[75] Inventors: Ronald Haselhorst, Lindenhurst; Tom Lillegard, Crystal Lake, both of Ill.

[73] Assignee: Clintec Nutrition Company, Deerfield, Ill.

[21] Appl. No.: 263,043

[22] Filed: Jun. 21, 1994

[51] Int. Cl.⁶ .................................................. A61M 25/00
[52] U.S. Cl. .......................... 604/283; 604/905; 285/177
[58] Field of Search .......................... 128/912; 285/177; 604/243, 256, 283, 326, 905

[56] References Cited

U.S. PATENT DOCUMENTS

| 4,257,629 | 3/1981 | Maple et al. | 285/12 |
|---|---|---|---|
| 4,511,163 | 4/1985 | Harris et al. | 285/177 |
| 4,692,150 | 9/1987 | Cianci et al. | 604/111 |
| 4,950,254 | 8/1990 | Anderson et al. | 604/247 |
| 4,969,879 | 11/1990 | Lichte | 604/283 |
| 5,049,139 | 9/1991 | Gilchrist | 604/265 |
| 5,057,093 | 10/1991 | Clegg et al. | |
| 5,267,983 | 12/1993 | Oilschlager et al. | |
| 5,275,447 | 1/1994 | McNab | 285/177 |
| 5,360,418 | 11/1994 | Weilbacher et al. | 604/283 |
| 5,399,173 | 3/1995 | Parks et al. | 604/282 |

*Primary Examiner*—Corrine M. McDermott
*Attorney, Agent, or Firm*—Hill, Steadman & Simpson

[57] ABSTRACT

An adapter is providing for connecting a fluid source to any one of a variety of tubes having variously sized access ports. The adapter has a body having a channel extending between two ends thereof. Along an exterior of the body, increased diameter sections are provided. Some of the increased diameter sections are tapered forming barbs around the periphery of the adapter. A method is further provided for connecting a fluid source to a variety of variously sized tubes.

5 Claims, 1 Drawing Sheet

ADAPTER FOR A VARIETY OF TUBES HAVING VARIOUS DIAMETERS AND A METHOD OF USING THE ADAPTER

BACKGROUND OF THE INVENTION

The present invention generally relates to adapters for mating a fluid source with a delivery tube. More specifically, the present invention relates to adapters for connecting an enteral fluid source to an enteral feeding device.

Infusion of nutritional formulations into a patient is, of course, generally known. Such nutritional products can be administered enterally or parenterally. One enteral means for providing such nutrition is by use of a feeding tube connected to a supply or source of a liquid nutritional product. A means for providing intravenous solution to a patient is via an intravenous (IV) needle, i.e. parenterally. The IV needle is inserted into a patient's venous system. A luer fit or other connection allows an adapter or coupler to be secured therein so that fluid can be infused through the needle into the patient.

It is also generally known to insert a catheter into a patient percutaneously or to use a nasogastric feeding tube. The catheter or tube is connected to a container holding a liquid nutritional product by a fluid conduit. Various sized adapters are normally provided at an outlet end of the fluid conduit. The adapters frictionally fit into an open end of the feeding catheter or tube.

An example of a multi-step adapter is disclosed in U.S. Pat. No. 5,057,093. Stepped adapters provide an outer surface having a series of stepped surfaces of progressively smaller diameter from the flow inlet of the adapter to the flow outlet of the adapter. Therefore, the adapter can be inserted into a wide variety of feed tubes and catheters of varying diameters and depths.

Another example of an enteral adapter is disclosed in U.S. Pat. No. 5,267,983. The adapter of the '983 patent again provides multi-steps for accommodating a wide range of diameters of access ports of enteral feeding devices. The leading step of the adapter is sized in length and diameter to prevent a secure connection to an IV access port.

These known adapters, however, have disadvantages. First, a secure, locking fit preventing separation of the adapter from the feeding tube cannot be guaranteed. A simple pulling or other external or internal force exerted on the feeding tube can result in releasing of the feeding tube from the adapter. To resolve this problem, often a separate locking mechanism or tethered member is connected to the adapter and/or the feeding tube to assist in preventing release of the feeding tube from the adapter.

A need, therefore exists for an improved adapter overcoming the deficiencies of known prior art adapters allowing a secure connection and a positive interference fit for any available tubes and/or catheter products.

SUMMARY OF THE INVENTION

The present invention provides an adapter for connecting a fluid source to a variety of tubes having various sized access ports. In addition, the present invention provides a method for connecting a first fluid conduit to a second fluid conduit enabling fluid communication therebetween.

In an embodiment, the present invention provides an adapter comprising a body having a channel therethrough. The channel is defined by a first opening at a first end and a second opening at a second end. The body has a plurality of sections wherein a first section has a first substantially uniform diameter section and a first tapering section; a second section has a second substantially uniform diameter section and a second tapering section wherein the second tapering section is longer than the first tapering section; and a third section has a third tapering section wherein the third tapering section is longer than the second tapering section. The first, second and third sections are integrally formed with the channel extending therethrough.

In an embodiment, the second tapering section of the adapter of the present invention has two different substantially uniform degrees of taper.

In an embodiment, the third tapering section of the adapter of the present invention has two different substantially uniform degrees of taper.

In an embodiment, the first tapering section of the adapter of the present invention has a shorter length than the first substantially uniform diameter section.

In an embodiment, the second opening of the adapter of the present invention has an increased diameter channel tapering from the second opening to a reduced diameter intermediate the first opening and the second opening.

In an embodiment, the second tapering section of the adapter of the present invention has a larger diameter than the first tapering section of the adapter of the present invention and a larger diameter than the second tapering section.

In an embodiment the adapter of the present invention further comprises a recessed area constructed and arranged at a point intermediate the first end and the second end of the body.

In another embodiment of the present invention, an adapter is provided for connecting a fluid source to a feed tube. The adapter comprises a body having a channel therethrough. The channel is defined by a first opening at a first end and a second opening at a second end. The body is integrally formed by, in sequential order from the first end to the second end, a first cylindrical segment, a first tapered segment, a second cylindrical segment, a second tapered segment and a third tapered segment wherein a diameter of the first tapered segment is larger than a diameter of the second cylindrical segment, the diameter of the second tapered segment is larger than the diameter of the third tapered segment.

In an embodiment, the first cylindrical segment of the adapter of the present invention is divided into two sections having a first diameter and a second diameter, respectively.

In an embodiment, the second tapered segment of the adapter of the present invention has two degrees of taper.

In an embodiment, the third tapered segment of the adapter of the present invention has two degrees of taper.

In an embodiment, the first cylindrical segment of the adapter of the present invention is longer than the first tapered segment.

In an embodiment, the second tapered segment of the adapter of the present invention is longer than the second cylindrical segment.

In an embodiment, a method is provided for connecting a tube to a fluid source. The method comprises the steps of: providing an adapter having an inlet port and an outlet port connected by a channel inside the adapter; providing an exterior of the adapter with a plurality of tapered segments and a plurality of cylindrical segments, the tapered segments having increased diameters as distance from the outlet ends increases and wherein at least one of the plurality of cylindrical segments is constructed and arranged between the plurality of tapered segments; and securing a second tube to the adapter at the outlet port.

In an embodiment, the method of the present invention further comprises the step of providing a recessed section opposite the outlet port of the adapter.

In an embodiment, the method of the present invention further comprises the step of providing a tapering connection at the inlet port.

In an embodiment, the method of the present invention further comprises the step of providing a gate having a diameter greater than the diameter of the largest tapered segment, the gate is constructed and arranged near the inlet end.

In an embodiment, the method of the present invention further comprises the step of providing non-uniform tapers in each of the plurality of tapered segments.

In an embodiment, the method of the present invention further comprises the step of increasing the length of the plurality of tapered segments as distance from the outlet end increases.

It is, therefore, an advantage of the present invention to provide an adapter and a method for connecting the adapter to any size tube.

Another advantage of the present invention is to provide an adapter and a method for using the adapter wherein the adapter provides an interlocking fit.

Still further, an advantage of the present invention is to provide an adapter and a method of using the adapter which interlocks from a slip connection.

Moreover, an advantage of the present invention is to provide an adapter and a method of using the adapter that is simple to implement.

And, another advantage of the present invention is to provide an adapter and a method of using same that is difficult to separate from a tubing at the outlet end.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an adapter that provides an interference fit and locking connection to a wide variety of feed tubes. Typical feed tubes for connection include, but are not limited to, enteral feeding devices, such as J-tubes and G-tubes, as well as Foley catheters.

Figure 1:
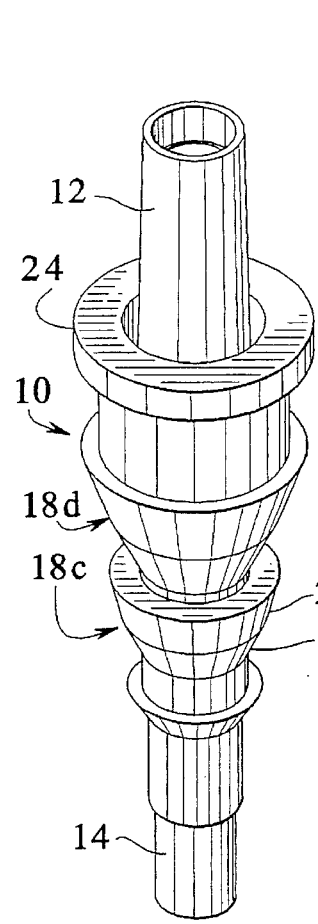
FIG. 1 illustrates a perspective view of an embodiment of the adapter of the present invention with feeding tubes connected at both the inlet and outlet ends of the adapter.

Referring now to the figures, FIG. 1 generally illustrates an adapter 10. The adapter 10 may be connected at each end by a length of tubing, such as a fluid conduit 12 and a feed tube 14, such as is generally known and used for enteral feeding. The fluid conduit 12 may be connected to, for example, an enteral fluid source (not shown), such as a feeding bag. The feed tube 14 may be attached to a second fluid conduit (not shown) leading directly into a gastro/intestinal system of a patient or the like. Alternatively, the feed tube 14 itself may lead into the patient's system. This arrangement allows fluid from the fluid source or other container to be infused into a patient. Of course, the fluid conduit 12 may be connected directly to the fluid source. Any number of known fluid sources may be implemented as will be appreciated by those skilled in the art.

Figure 2:
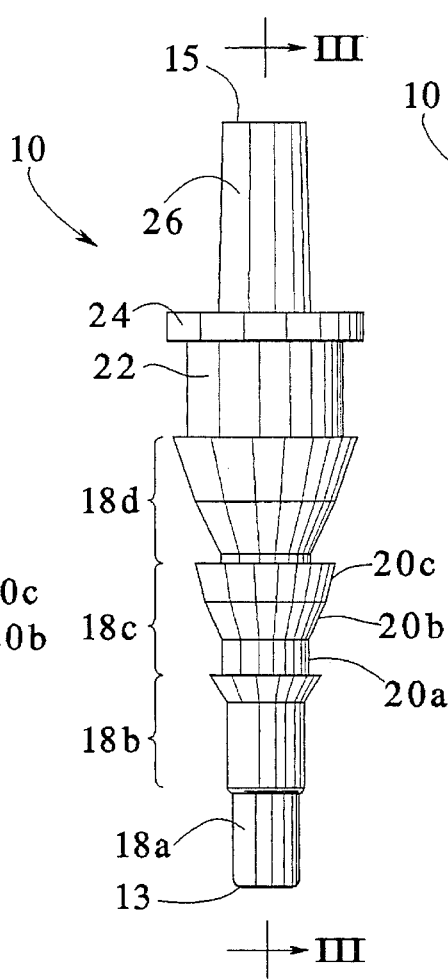
FIG. 2 illustrates a plan view of an embodiment of the adapter of the present invention.
Figure 3:
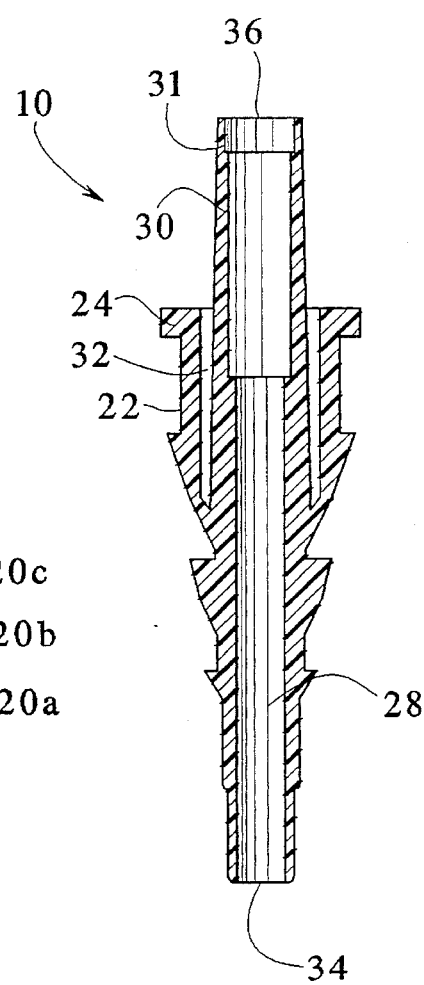
FIG. 3 illustrates a cross-sectional view of the adapter illustrated in FIG. 2 taken generally along the line III—III of the adapter of the present invention.

As more clearly illustrated in FIGS. 2 and 3, the adapter 10 has a plurality of sequentially stepped diameter forming sections 18a, 18b, 18c and 18d. The sections 18a, 18b, 18c and 18d are arranged from an output end 13 of the adapter 10 to which the feed tube 14 may be connected to an input end 15. The sections 18a 18b, 18c and 18d are arranged to provide an increasing diameter from the output end 13 to the input end 15.

In the presently preferred embodiment of the adapter 10, the first section 18a has a length of approximately 0.238" and a diameter of 0.180". The second section 18b has a length of approximately 0.329" with a uniform radius of 0.242" for a portion of the length that tapers to a radius of 0.323" in the remaining portion. The smaller radius is provided substantially throughout the second section 18b. The last 0.25" of the second section 18b is tapered at an angle of approximately 25°. Both the first section 18a and the second section 18b have radiused corners to assist in receiving the feed tube 14. The radiused corners allow for the feed tube 14 to be slipped onto the adapter 10 with application of minimal forces.

The third section 18c is approximately 0.292" in length and is divided into three substantially equivalent sub-sections 20a, 20b and 20c. The first sub-section 20a of the third section 18c has a substantially equivalent diameter throughout of approximately 0.260". The length of the sub-section 20a is approximately 0.079" or one-third of the length of the third section 18c. A taper begins on an exterior portion of the adapter 10 following the first sub-section 20a. The taper continues for the remainder of the third section 18c with a slightly reduced taper beginning between the sub-sections 20b and 20c. At the end of the third sub-section 20c, a radiused corner is provided leading into the fourth section 18d.

The fourth section 18d has a radiused corner at the junction of the fourth section 18d with the third section 18c. The length of the fourth section 18d is approximately 0.330" and is substantially evenly tapered following the radiused corner to an opposite end of the fourth section 18d. The taper is slightly reduced at an approximate midpoint intermediate the ends of the fourth section 18d. The radius at an end is approximately 0.510" and at its narrowest portion approximately 0.272". Following the widest point of the fourth section 18d, the adapter 10 has a reduced diameter section 22 of a substantially equivalent diameter of approximately 0.440". The reduced diameter section 22 has a length of approximately 0.263". Following the reduced diameter section 22 is a sub-gate section 24 of substantially equivalent diameter slightly larger than the reduced diameter section 22 and approximately 0.546". The sub-gate section 24 extends for approximately 0.080". The sub-gate section 24 provides a gripping surface for holding the adapter 10 and for assisting in insertion of the adapter 10 into the feed tube 14.

Finally, a fluid conduit receiving section 26 is provided at the inlet end 15 opposite the first section 18a at the outlet end 13. The fluid conduit section 26 has a substantially uniform exterior diameter of approximately 0.240". The length of the fluid conduit section 26 is approximately 0.5".

Referring now to FIG. 3, an interior passageway 28 is provided through the length of the adapter 10. The interior passageway is defined by a first opening 34 at the outlet end 13 and a second opening 36 at the inlet end 15. The interior passageway 28 has a substantially equivalent diameter of approximately 0.102" through the sections 18a, 18b, 18c and 18d. At a point in the interior passageway 28 intermediate the inlet end 15 and the outlet end 13, the diameter of the interior passageway 28 is widened to approximately 0.146" and a taper extends through the fluid conduit section 26 and the interior passageway 28 resulting in the second opening 36 at the inlet end 15 of approximately 0.194" in diameter.

At the inlet end 15 of the interior passageway 28 within the fluid conduit section 26, a taper 30 is provided. The taper 30 has a widened diameter opening 31 at the inlet end of 15 prior to the taper 30. The opening 31 is substantially uniform in diameter. The opening 31 and the taper 30 provide a means for attaching, for example, a needle or cannula or the like providing a sealed relationship therebetween.

The adapter 10 is further provided with a recessed area 32 extending peripherally around the sub-gate section 24, the reduced diameter section 22 and into the fourth section 18d. The recessed area 32 provides an area for which a larger tubing or other fluid conduit may be connected at the inlet end 15 of the adapter 10, such as illustrated in FIG. 1.

Figure 4:
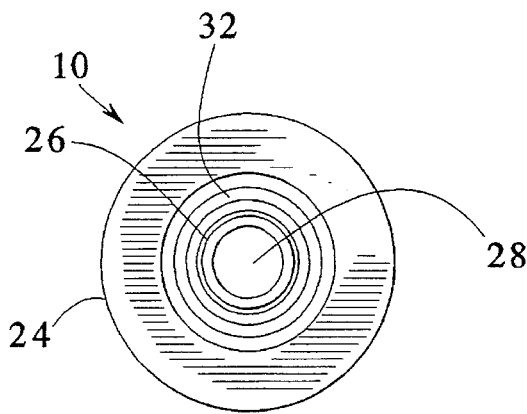
FIG. 4 illustrates a top plan view of an embodiment of the adapter of the present invention.
Figure 5:
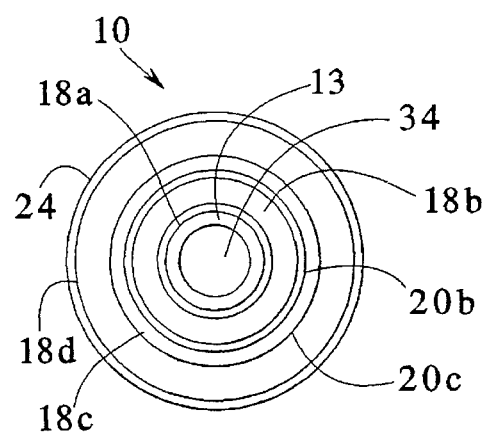
FIG. 5 illustrates a bottom plan view of an embodiment of the adapter of the present invention.

FIGS. 4 and 5 illustrate top plan and bottom plan views, respectively, of the adapter 10. The numerical labelling of each of FIGS. 4 and 5 corresponds to diameters of each of the respective sections of the adapter 10 described with reference to FIG. 1–3.

The construction of the adapter 10 allows for any fluid conduit to be secured to the adapter 10. The adapter 10, therefore, allows a fluid container to be placed in fluid communication with effectively any type of enteral feeding device, including, but not limited to, G-tubes, J-tubes, Foley catheters, and the like. The adapter 10 is particularly suitable for use with enteral feeding devices having annular rings. The sections of the adapter 10 of the present invention are constructed and arranged to lock into the annular rings providing a secure fit for the feeding tube set.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. An adapter for connecting a fluid source to a feed tube, the adapter comprising:

a body having a channel therethrough, the channel defined by a first opening at a first end and a second opening at a second end, the body integrally formed by, in continuous and sequential order from the first end to the second end, a first continuously uniform cylindrical segment, a first tapered segment, a second continuously uniform cylindrical segment, a second tapered segment and a third tapered segment wherein a diameter of the first tapered segment is larger than a diameter of the second cylindrical continuously uniform segment and further wherein a diameter of the second tapered segment is larger than a diameter of a junction between the second tapered segment and the third tapered segment wherein the first continuously uniform cylindrical segment is divided in two sections having a first diameter and a second diameter in continuous and sequential order from the first end to the second end, respectively, wherein the first diameter is smaller than the second diameter of the first continuously uniform cylindrical segment.

2. The adapter of claim 1 wherein the second tapered segment has two degrees of taper.

3. The adapter of claim 1 wherein the third tapered segment has two degrees of taper.

4. The adapter of claim 1 wherein the first cylindrical segment is longer that the first tapered segment.

5. The adapter of claim 1 wherein the second tapered segment is longer than the second cylindrical segment.

* * * * *